United States Patent [19]

Hanefeld et al.

[11] Patent Number: 4,643,997

[45] Date of Patent: Feb. 17, 1987

[54] 3-CARBAMOYL- AND 3-THIOCARBAMOYL-TETRAHYDRO-1,3-THIAZINE-2-THIONES AND SKIN TREATING COMPOSITIONS CONTAINING THE SAME

[75] Inventors: Wolfgang Hanefeld, Marburg, Fed. Rep. of Germany; Rudi Röthlisberger, Marly; Friedrich Noser, Bonnefontaine, both of Switzerland

[73] Assignee: Wella Aktiengesellschaft, Darmstadt, Fed. Rep. of Germany

[21] Appl. No.: 694,643

[22] Filed: Jan. 24, 1985

[30] Foreign Application Priority Data

Jan. 31, 1984 [DE] Fed. Rep. of Germany ....... 3403147

[51] Int. Cl.⁴ .................... A01N 1/02; C07D 279/06; A61K 7/48; A61K 7/42
[52] U.S. Cl. ........................................ 514/226; 544/3; 544/54; 424/59; 540/467; 540/470; 540/481; 540/544; 540/553; 540/575; 540/598
[58] Field of Search ................... 260/243.3; 514/226; 544/54, 3; 424/59

[56] References Cited

U.S. PATENT DOCUMENTS

| | | | |
|---|---|---|---|
| 4,256,481 | 3/1981 | Gardi et al. | 544/54 |
| 4,268,264 | 5/1981 | Grollier et al. | 8/410 |
| 4,432,769 | 2/1984 | Bugaut et al. | 8/414 |

OTHER PUBLICATIONS

CRC Handbook of Chemistry and Physics (60th Ed) 1980, pp. C33–C36.

*Primary Examiner*—John M. Ford
*Attorney, Agent, or Firm*—Michael J. Striker

[57] ABSTRACT

New 3-carbamoyl- and 3-thiocarbamoyl-tetrahydro-1,3-thiazine-2-thiones are disclosed as skin treatment compositions based upon physiologically-compatible carriers and a content of these compounds as active substance for increasing the skin protection, in particular against sun radiation and contact with environmental substances of all types. The skin treatment compositions are also suitable for prophylactic control of so-called aging skin. The compositions are applied to the skin one or two times daily for about 3-4 weeks.

16 Claims, No Drawings

3-CARBAMOYL- AND 3-THIOCARBAMOYL-TETRAHYDRO-1,3-THIAZINE-2-THIONES AND SKIN TREATING COMPOSITIONS CONTAINING THE SAME

BACKGROUND OF THE INVENTION

The skin forms the limiting layer between the organism and its environment. The most important object of the skin is to protect the interior of the body against exogenous influence. The skin comes into contact daily with foreign-to-body substances, in part hostile to a body, and specifically, hostile to the skin. Particularly frequent contact of the unprotected skin with these substances, which is often conditioned upon occupation (hairdressers, housewives, dentists), therefore leads sooner or later to more or less serious skin injuries. In order to avoid or at least to decrease the skin injuries, previously two principal types of measure have been introduced, indeed a protective skin cover as well as conserving skin care.

The protective skin cover involves treating the skin before contact with the foreign-to-the-skin substances in order to thereby extensively avoid direct contact between the skin surface and the harmful substances. The preparations which assure a protective skin cover work by chemical-physical activity, without invading into the physiology of the skin. Such preparations must particularly fulfill the following requirements: they should be impermeable and insoluble with regard to most exogenous substances; they should display a good skin compatibility; they should be easy to apply and also to remove again from the skin surface; they should not impair the grip of the hands and thereby their workability; and should display a certain maintenance duration. The disadvantage of the known preparations of this type is that they are not capable of optimally fulfilling all of these requirements. With the so-called conserving skin treatment, the skin is made less susceptible upon contact with the substances harmful to the skin. The skin cover substances are already contained in washing agents. One distinguishes their activities by various types of skin protection measures, and indeed such measures which act by means of absorption into the skin surface, refatting measures, acidifying measures and degelling measures. Here, too, the essential disadvantage of these skin protection meaures in that they are not effective in equal manner against all aggressions of the various environmental substances.

SUMMARY OF THE INVENTION

In contrast thereto, all of the requirements which are placed upon a skin protection preparation will be fulfilled, as a result of its new type of activity, by skin treatment compositions having a content of 3-carbamoyl- and 3-thiocarbamoyl-tetrahydro-1-3-thiazine-2-thione of the general formula (I)

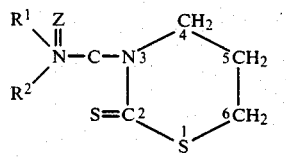

whereby Z signifies oxygen or sulphur and $R^1$ and $R^2$ are the same or different and are each alkyl, hydroxyalkyl, carboxyalkyl, halogen alkyl, cyanoalkyl, alkoxyalkyl, cycloalkyl, alkenyl, alkinyl, arylalkyl, arylalkyl with substituted aryl, aryl-, alkyl-, halogen-, nitro-, alkoxy-, aryloxy-, cyano-substituted aryl, thiazolyl, thienyl, benzthiazolyl, thiadiazolyl, oxazolyl, benzoxazolyl, oxydiazolyl, pyrazolyl, triazolyl, bezimidazolyl, pyridinyl, pyrimidinyl, purinyl, pyridazinyl, triazinyl, benzotriazinyl, quinolyl, isoquinolyl, cinnolinyl, phthalazolyl, pteridinyl, quinoxazinyl or acridinyl, or $R^1$ and $R^2$ together with the nitrogen atom to which they are bound are part of a heterocyclic ring containing the segment $-(CH_2)_n-X-(CH_2)_m-$, with X being $CH_2$, O, S or NR', whereby R' is alkyl, arylalkyl or aryl, and n is 0 to 3 and m is 1 to 3, with the proviso that n is only 0 when X is $CH_2$.

The subject of the present invention is therefore a skin composition, containing physiologically compatible carrier and additives, characterized by a content of at least one compound of the above given general formula I.

The skin treatment composition according to the present invention can be provided in optional forms of preparation, suitable for skin treatment compositions, such as for example, as clear, colored or cloudy solutions, as dispersions, emulsions, in the form of a foam or even as a preparation to be sprayed from an aerosol container by means of a pump or by means of a propellant gas. Preferably, however, they are provided as salves, creams or gels. Coming into consideration as examples for preparations according to the present invention, are, particularly, cosmetic skin treatment compositions, such as day creams, night creams, nutrient creams, skin creams, skin protection creams, sun protection creams, sun protection sprays, as well as moreover, lipsticks, skin milk preparations, skin lotions and skin protection gels.

The concentration of the compounds of general formula I in the skin treatment compositions amounts in total about 0.1 up to 5% by weight, preferably 0.5 up to 3% by weight. Herewith the compounds of formula I can be provided alone, or in mixture with one another in the compositions.

The composition of the skin treatment compound represents a mixture of the compounds according to formula I with the physiologically components customary for such preparations, such as carriers and additives.

Customary carriers and additives in solutions, creams, emulsions or gels are, for example, solvents, such as water, lower aliphatic alcohols, for example ethanol, propanol, or isopropanol or glycols such as glycerine and propylene glycol, moreover wetting agents or emulsifiers from the classes of anionic, cationic, amphoteric or non-ionogenic surface-active substances such as fatty alcohol sulfate, alkyl sulfonate, alkyl benzene sulfonate, alkyl trimethylammonium salt, alkyl betaine, oxyethylated fatty alcohol, oxyethylated nonylphenol, fatty acid alkanol amide, oxyethylated fatty acid ester, moreover thickneners such as fatty alcohol, fatty acid ester, starch, cellulose derivative, petroleum, stearin, ceresin, paraffin oil and fatty acids, as well as moreover, care substances such as lanolin, lanolin derivatives, cholesterin, pantothenic acid, sorbite, betaine, almond oil, avocado oil, beeswax and spermacetti.

Further customary additives are, for example, cosmetic resin, dyes, perfume oils, propellant gas as well as conserving substances, such as for example, p-hydroxybenzoic acid, sorbic acid, salicylic acid, formaldehyde and hexachlorophene. For salt formation the compositions can contain base, such as for example, triethanolamine.

The preparation of the skin treatment composition follows in the manner customary for such preparations, in that the compound or compounds of formula I serving as active substance, are intermixed with the components serving as carrier for the skin treatment composition, and thereafter the mixture is filled with the further components of the composition, into the prepared final product. The compounds of general formula I contained as components of the here described skin treatment composition, effect a thickening of the outermost skin layer, known as the dead horny layer, after repeated epicutaneous treatment, which layer is responsible in the first instance for natural skin protection. By means of this thickening of the horny layer, the skin is made more resistant against contact with environmental substances of all types, and forms in this manner an optimal skin protection. Since the skin protection which is assured by means of these compounds resides in a strengthening of the natural skin protection, the skin protection composition according to the present invention, which contains compounds according to general formula I, does not display the disadvantages which are observed with the conventional skin protection compositions. The skin treatment composition according to the present invention can be applied periodically to the skin surface, independent of contact with the foreign-to-the-skin substances. They therefore never disturb a work operation, since they are no longer located on the skin surface at this point in time. The skin protection can also not be removed (for example, by means of washing), since it is indeed obtained by means of the new state of the skin (thickened). Simultaneously, the compounds of the general formula I effect a strengthening of the natural sun protection. This additional sun protection is likewise obtained by means of the thickening of the horny layer which is realized after the treatment with the skin treatment composition according to the present invention. A thickening of the horny layer effects mainly an increased absorption of light and sun radiation. This new type of prophylactic sun protection (pre-sun) displays clear advantages compared with the effectiveness obtainable with the convention sun protection compositions. The customary sun protection composition is applied to the surface of the skin and therewith its absorptive capacity, i.e., its light protectiveness, depends upon the applied layer thickness. These preparations can be disturbing, in that they for example, are too strongly fatty and thereby dirty clothing. They are rinsed off, for example, by means of bathing or showering and must therefore constantly be reapplied. In contrast thereto, the composition according to the present invention can be periodically applied independent of the exposure to the sun, for example, they can be repeatedly applied epicutaneously, indeed 3-4 weeks before the summer vacation, so that they then offer at vacation time, as a result of the thickened horny layer, indeed a long-lasting, non-washable protection from sunburn and other serious light injuries.

With advancing age, the outer layer of the skin, i.e., the so-called overskin or epidermis, becomes thinner. The thinning of the epidermis is therefore responsible for the skin surface obtaining with age its typical parchment-like appearance, and for sebaceous glands, retention cysts, pigment flecks as well as fine blood vessels becoming more visible and marking the typical quality of a so-called aging skin. Insofar as the composition according to the present invention is capable of thickening not only the horny layer, which indeed represents only a part of the epidermis, but the entire epidermis, it represents an effective agent for the prophylatic treatment of skin aging.

The skin treatment composition according to the present invention is expediently employed in such manner that, beginning about 3-4 weeks before the point in time at which a thickening of the horny layer respectively the epidermis should be provided, is repeatedly and preferably one to two times daily, applied to the appropriate areas of the skin.

The skin thickening activity of the compounds according to the present invention is proven in the following manner with hairless mice:

2% by weight of each of the compounds a through e infra are applied epicutaneously in the form of a 50% by volume ethanolic solution, daily, aside from Saturday and Sunday during a 2-week period, to one body side of hairless mice (HR/HR). At the end of the treatment period, the animals are put to death and from both body sides of each animal a skin surface about $1 \times 1.5$ cm size is removed and worked up histologically. The thickness of the epidermis is measured at about one hundred places, and the average skin thickness is determined. The thickening of the epidermis can then be obtained by means of the quotient of the average thickness of the treated epidermis and the average thickness of the untreated epidermis. This quotient is designated the thickening factor. The compounds according to the present invention provide thickening factors lying between 1.3 and 1.7.

The compounds according to the present invention of formula I are new. Of these new compounds those which are particularly suitable for skin treatment are of general formula II

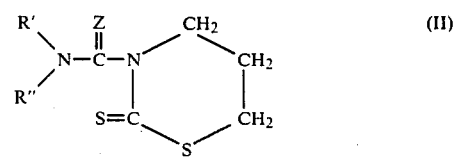

in which R' and R'' are the same or different and are each alkyl, aryl alkyl or aryl, and Z is oxygen or sulphur.

Specific examples of compounds according to the present invention are:
(a) 3-(dimethylcarbamoyl)-tetrahydro-1,3-thiazine-2-thione
(b) 3-(diphenylcarbamoyl)-tetrahydro-1,3-thiazine-2-thione
(c) 3-(dimethylthiocarbamoyl)-tetrahydro-1,3-thiazine-2-thione
(d) 3-(diethylthiocarbamoyl)-tetrahydro-1,3-thiazine-2-thione
(e) 3-(dibenzylthiocarbamoyl)-tetrahydro-1,3-thiazine-2-thione The preparation of the compounds according to formula I follows according to the following reaction equations by means of several hours heating of tetrahydro-1,3-thiazine-2-thione (III) with an equivalent or somewhat excess molar amount of a carbamoyl- or thiocarbamoyl chloride (IV) in the presence of a an equimolar or somewhat excess molar amount of a tertiary amine, preferably triethylamine, in dry toluene.

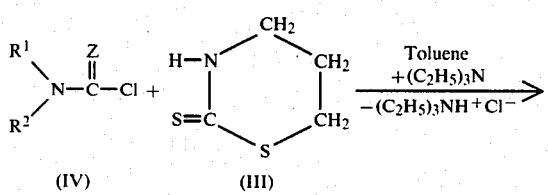

(IV)  (III)  (I)

The tetrahydro-1,3-thiazine-2-thione (III) is obtainable either from 3-bromopropylamine-hydrobromide, caustic soda and carbon disulfide (S. Gabriel, W. E. Lauer, Report of the German Chemical Industry, Vol. 23 (1890), p. 87) or from 3-aminopropanol, carbon disulfide and caustic soda after acidification (Diamond Alkali Company, U.S. Pat. No. 2,845,339; C.A.52, 19003 [1958]). Carbamoyl- respectively thiocarbamoyl chloride are accessible by various processes (C. Ferri, Reactions of Organic Synthesis, pp. 142, 636, 641; George Thieme Verlag, Stuttgart, 1978).

In analogous manner, according to the above described process for production of compounds according to the general formula I unsubstituted in the ring positions 4, 5 and 6, also the compounds of general formula V substituted in these positions can be prepared from the correspondingly substituted tetrahydro-1,3-thiazine-2-thiones,

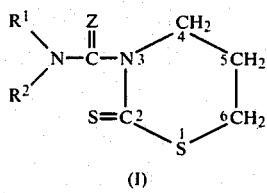

(V)

whereby Z, $R^1$ and $R^2$ have the same meaning as in formula I, $R^3$ is H, OH, alkyl, substituted alkyl, aryl, substituted aryl, arylalkyl, arylalkyl substituted in the aryl part, amino, monoalkyl amino or dialkyl amino, $R^4$ is H, alkyl, substituted alkyl, aryl, substituted aryl, aryl alkyl, aryl alkyl substituted in the aryl part, $R^5$ is H, alkyl or OH, $R^6$ is H or alkyl, $R^7$ is H, alkyl or aryl, and $R^8$ is H, alkyl, substituted alkyl, hydroxy, mercapto, amino, monoalkyl amino or dialkyl amino.

Tetrahydro-1,3-thiazine-2-thione substituted in positions 4, 5 and 6, which is suitable for reaction with carbamoyl chloride, respectively thiocarbamoyl chloride into the compounds of general formula V, is known from the literature. Thus, for example, the preparation of 4-methyl-tetrahydro-1,3-thiazine-2-thione is described by J. L. Garraway, J. Chem. Soc. (B) (1966), p. 99. Moreover, the 4-hydroxy-4,6,6-trimethyl-tetrahydro-1,3-thiazine-2-thione can be obtained according to J. E. Jansen and R. A. Mathes, J. Am. Chem. Soc. Vol. 77 (1955), p. 2866, and the 6-isopropylamino-4,4,6-trimethyl-tetrahydro-1,3-thiazine-2-thione can be obtained according to K. Schreiber, A. Fuchsberger, and G. Zigeuner, Monatsheft der Chimie 108 (1977), p. 257.

The novel features which are considered characteristic for the invention are set forth in particular in the appended claims. The invention itself, however, both as to its construction and as to its method of operation, together with additional objects and advantages thereof, will be best understood from the following description of specific embodiments.

DESCRIPTION OF THE PREFERRED EMBODIMENTS

PRODUCTION EXAMPLES

For the production of 3-carbamoyl- respectively 3-thiocarbamoyl-tetrahydro-1,3-thiazine-2-thione of formula I, per apparatus initially 1.34 g (0.01 Mol) tetrahydro-1,3-thiazine-2-thione and 1.0 g (0.01 Mol) triethyl amine are dissolved under heating in 20 g dry toluene. After addition of 0.01 Mol of the particular carbamoyl- or thiocarbamoyl-chloride of formula IV, the reaction mixture is heated to boiling for about 6–24 hours, with stirring, then cooled down, and worked up as follows, according to the desired final product:

EXAMPLE 1

3-(dimethylcarbamoyl)-tetrahydro-1,3-thiazine-2-thione

The sediment obtained after cooling down is filtered, and then washed first with a mixture of dioxane/toluene (1:1) and subsequently several times with water for removal of the triethyl amine-hydrochloride. The so-washed product is recrystallized from toluene. Melting point of the colorless crystals: 138°–139° C. Yield: 64% of theoretical amount.

| SN-Analysis: | | % N | % S |
|---|---|---|---|
| ($C_7H_{12}N_2OS_2$) | calculated | 13.72 | 31.39 |
| (MW = 204.32) | found | 13.64 | 31.31 |
| Infrared absorption bands: | 1700 cm$^{-1}$ | (C=O) | |
| | 1485 cm$^{-1}$ | (N—C—S) $\underset{S}{\overset{\|}{\phantom{.}}}$ | |

EXAMPLE 2

3-(diphenylcarbamoyl)-tetrahydro-1,3-thiazine-2-thione

The colorless crystals obtained after cooling down are filtered off, and then washed several times with water. The undissolved portion is recrystallized from toluene. Melting point: 226°–228° C. Yield: 66% of theoretical.

| SN-Analysis | | % N | % S |
|---|---|---|---|
| ($C_{17}H_{16}N_2OS_2$) | calculated | 8.53 | 19.52 |
| (MW = 328.46) | found | 8.51 | 19.59 |
| Infrared absorption bands: | 1700 cm$^{-1}$ | (C=O) | |
| | 1490 cm$^{-1}$ | (N—C—S) $\underset{S}{\overset{\|}{\phantom{.}}}$ | |

EXAMPLE 3

3-(dimethylthiocarbamoyl)-tetrahydro-1,3-thiazine-2-thione

The colorless crystals obtained after cooling down are filtered off, and then washed several times with water, after which the undissolved portion is recrystallized from methylene chloride. Melting point: 209°–211° C. Yield: 64% of theoretical.

| SN-Analysis | | % N | % S |
|---|---|---|---|
| ($C_7H_{12}N_2S_3$) | calculated | 12.71 | 43.65 |
| (MW = 220.38) | found | 12.54 | 43.45 |

Infrared absorption bands: 1530–1550 cm$^{-1}$ (N—C=S).

EXAMPLE 4

3-(diethylthiocarbamoyl)-tetrahydro-1,3-thiazine-2-thione

After cooling down, the toluene is completely removed under vacuum, the residue is agitated with methylene chloride/water, the methylene chloride phase is dried across sodium sulfate, compressed in a vacuum and the residue is recrystallized from methylene chloride/ether. Melting point: 118°–120° C. Yield: 73% of theoretical amount.

| SN-Analysis | | % N | % S |
|---|---|---|---|
| ($C_9H_{16}N_2S_3$) | calculated | 11.28 | 38.72 |
| (MW = 248.43) | found | 11.22 | 38.92 |

Infrared absorption bands: 1525 cm$^{-1}$ (N—C=S).

EXAMPLE 5

3-(dibenzylthiocarbamoyl)-tetrahydro-1,3-thiazine-2-thione

After cooling down, the triethylamine-hydro chloride is filtered off, the filtrate is completely compressed in a vacuum and the residue is agitated with methylene chloride/water. The methylene chloride phase is then dried over sodium sulfate and after addition of ether, colorless crystals separate. Melting point: 175°–176° C. Yield: 48% of theoretical amount.

| SN-Analysis | | % N | % S |
|---|---|---|---|
| ($C_{19}H_{20}N_2S_3$) | calculated | 7.52 | 25.82 |
| (MR = 372.58) | found | 7.40 | 25.57 |

Infrared absorption bands: 1505 cm$^{-1}$ (N—C=S).

EXAMPLES FOR SKIN TREATMENT COMPOSITIONS

Preparation for Skin Protection

| EXAMPLE 6: Cream | |
|---|---|
| 2.0 g | 3-(dibenzylthiocarbamoyl)-tetrahydro-1,3-thiazine-2-thione |
| 6.0 g | mixture of 60 wt % glycerin monostearate and 40 wt % glycerindistearate |
| 4.0 g | polyoxyethyleneglycerin monostearate |
| 3.0 g | cetylalcohol |
| 2.0 g | paraffin oil, viscous |
| 1.0 g | lanolin |
| 0.3 g | perfume and conserving agent |
| 81.7 g | water |
| 100.0 g | |

| EXAMPLE 7: Lotion | |
|---|---|
| 1.5 g | 3-(dimethylthiocarbamoyl)-tetrahydro-1,3-thiazine-2-thione |
| 0.5 g | isopropyl lanolate |
| 3.0 g | stearic acid, pressed three times |
| 2.0 g | glycerin monostearate |
| 1.0 g | triethanolamine |
| 0.3 g | perfume and conserving agent |
| 91.7 g | water |
| 100.0 g | |

Pre-sun Preparations (Sun Protection Compositions)

| EXAMPLE 8: Milk | |
|---|---|
| 2.5 g | 3-(diphenylcarbamoyl)-tetrahydro-1,3-thiazine-2-thione |
| 3.0 g | cetylphosphoric acid-diethanolamine salt |
| 3.0 g | stearic acid, pressed three times |
| 5.0 g | isopropyl palmitate |
| 5.0 g | paraffin oil, thin liquid |
| 0.5 g | perfume and conserving agent |
| 81.0 g | water |
| 100.0 g | |

| EXAMPLE 9: Body Lotion | |
|---|---|
| 2.0 g | 3-(dimethylcarbamoyl)-tetrahydro-1,3-thiazine-2-thione |
| 6.6 g | propyleneglycol mono- and distearate, not self-emulsifying (monostearate content 60%) |
| 1.4 g | triethanolamine |
| 1.0 g | lanolin |
| 2.0 g | isopropyl myristate |
| 2.0 g | 2-octyldodecanol |
| 5.0 g | avocado oil |
| 2.6 g | stearic acid, pressed three times |
| 0.6 g | oleic acid |
| 3.0 g | sorbite |
| 0.5 g | perfume and conserving agent |
| 73.3 g | water |
| 100.0 g | |

Preparations for Prophylactic Treatment of Aging Skin

| EXAMPLE 10: Night Cream | |
|---|---|
| 1.5 g | 3-(dimethylcarbamoyl)-tetrahydro-1,3-thiazine-2-thione |
| 22.0 g | lanolin alcohol fractions |
| 5.0 g | isopropyl myristate |
| 3.0 g | ceresin (paraffinum solidum) |
| 3.0 g | lanolin |
| 5.0 g | glycerin |
| 0.5 g | perfume and conserving agent |
| 60.0 g | water |
| 100.0 g | |

| EXAMPLE 11: Face and Neck Cream | |
|---|---|
| 2.0 g | 3-(diethylthiocarbamoyl)-tetrahydro-1,3-thiazine-2-thione |
| 3.0 g | cetylphosphoric acid-diethanolamine salt |
| 5.0 g | stearic acid, pressed three times |
| 15.3 g | almond oil |
| 10.0 g | isopropyl palmitate |
| 5.0 g | lanolin |
| 0.6 g | perfume and conserving agent |
| 59.1 g | water |
| 100.0 g | |

It will be understood that each of the elements described above, or two or more together, may also find a useful application in other types of skin compositions differing from the types described above.

While the invention has been illustrated and described as embodied in 3-carbamoyl- and 3-thiocarbamoyl-tetrahydro-1,3-thiazine-2-thiones, process for the production thereof and skin treating compositions containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Tetrahydro-1,3-thiazine-2-thione derivative of the formula:

$$\begin{array}{c} R' \\ \diagdown \\ R'' \end{array} N - \overset{Z}{\underset{\|}{C}} - N \begin{array}{c} CH_2 \\ \diagdown \\ CH_2 \\ \diagup \\ CH_2 \end{array}$$
$$S = C \diagdown_S \diagup$$

wherein,
R' and R'' are the same or different and are each independently selected from the group consisting of a lower alkyl, a phenylalkyl and a phenyl; and
Z is a member selected from the group consisting of oxygen and sulfur.

2. The compound according to claim 1, wherein R' is an alkyl having from 1 to 3 carbon atoms.

3. The compound according to claim 1, wherein R'' ia an alkyl having from 1 to 3 carbon atoms.

4. 3-(Dimethylcarbamoyl)-tetrahydro-1,3-thiazine-2-thione.

5. 3-(Diphenylcarbamoyl)-tetrahydro-1,3-thiazine-2-thione.

6. 3-(Dimethylthiocarbamoyl)-tetrahydro-1,3-thiazine-2-thione.

7. 3-(Diethylthiocarbamoyl)-tetrahydro-1,3-thiazine-2-thione.

8. 3-(Dibenzylthiocarbamoyl)-tetrahydro-1,3-thiazine-2-thione.

9. A skin treatment composition comprising, in a physiologically compatible carrier, a content of at least, one tetrahydro-1,3-thiazine-2-thione derivative of the formula:

$$\begin{array}{c} R^1 \\ \diagdown \\ R^2 \end{array} N - \overset{Z}{\underset{\|}{C}} - N \begin{array}{c} CH_2 \\ 3 \quad 4 \quad 5 CH_2 \\ \diagup \\ 6 CH_2 \end{array}$$
$$S = C^2 \diagdown_S \diagup^1$$

in which Z signifies a member of the group of oxygen and sulfur; $R^1$ and $R^2$ are the same or different and are each a member independently selected from the group consisting of a lower alkyl, a lower hydroxyalkyl, a lower carboxyalkyl, a lower halogenalkyl, a lower cycloalkyl, a lower alkenyl, a lower alkinyl, a lower cyanoalkyl, a phenylalkyl with a lower alkyl, an alkoxyalkyl with a lower alkyl, a phenyl-, alkyl-, halogen-, nitro-, alkoxy-, phenyloxy- and cyano-substituted phenylalkyl with a lower alkyl, a phenyl or an aromatic heterocyclic compound selected from the group consisting of thiazolyl, thienyl, benzothiazolyl, thiadiazolyl, oxazolyl, benzoxazolyl, oxadiazolyl, pyrazolyl, triazolyl, benzimidazolyl, pyridinyl, pyrimidinyl, purinyl, pyridazinyl, triazinyl, benzotriazinyl, quinolyl, isoquinolyl, cinnolinyl, phthalazolyl, pteridinyl, quinoxazinyl and acridinyl, or $R^1$ and $R^2$ together with the nitrogen atom to which they are bound are part of a non-aromatic heterocyclic ring containing the segment $-(CH_2)_n-X-(CH_2)_m-$, in which X is a member selected from the group consisting of $CH_2$, O, S and NR' wherein R' is a member selected from the group consisting of an alkyl, a phenylalkyl and a phenyl, and m is an integer of 1 to 3 and n is 0 or an integer of 1 to 3, with the proviso that n is only 0 when X is $CH_2$.

10. The composition according to claim 9, wherein said compound or compounds of formula I are contained in an amount of 0.1 up to 5% by weight.

11. The composition according to claim 9, wherein said compound or compounds of formula I are present in an amount of 0.5 up to 3% by weight.

12. The composition according to claim 9, in the form of a cream.

13. The composition according to claim 9, wherein the tetrahydro-1,3-thiazine-2-thione derivative is one where $R^1$ and $R^2$ are an alkyl group having from 1 to 3 carbon atoms.

14. The composition according to claim 9, wherein the tetrahydro-1,3-thiazine-2-thione derivative is one where $R^1$ and $R^2$ are a phenylalkyl group with an alkyl chain having from 1 to 3 carbon atoms.

15. The composition according to claim 9, wherein the tetrahydro-1,3-thiazine-2-thione derivative is one where $R^1$ and $R^2$ are a phenyl group.

16. The composition according to claim 9, wherein the thiazinethione is one where $R^1$ is an alkyl group having from 1 to 3 carbon atoms.

* * * * *